US007449299B2

(12) United States Patent
Bauer

(10) Patent No.: US 7,449,299 B2
(45) Date of Patent: Nov. 11, 2008

(54) QUANTUM DOT NANOPARTICLE-BASED UNIVERSAL NEUROTOXIN BIOSENSOR

(76) Inventor: David Bauer, 5700 Arlington Ave., #15F, Bronx, NY (US) 10471

( * ) Notice: Subject to any disclaimer, the term of this patent is extended or adjusted under 35 U.S.C. 154(b) by 0 days.

(21) Appl. No.: 11/684,109

(22) Filed: Mar. 9, 2007

(65) Prior Publication Data
US 2007/0212746 A1 Sep. 13, 2007

Related U.S. Application Data

(60) Provisional application No. 60/781,096, filed on Mar. 10, 2006.

(51) Int. Cl.
*C12Q 1/68* (2006.01)
*G01N 33/53* (2006.01)
*G01N 33/543* (2006.01)

(52) U.S. Cl. .................. 435/6; 435/4; 435/17; 436/518

(58) Field of Classification Search ........................ None
See application file for complete search history.

(56) References Cited

U.S. PATENT DOCUMENTS

| 1,344 | A * | 9/1839 | Brown .......................... 114/53 |
| 6,821,738 | B2 * | 11/2004 | Harmon ....................... 435/7.1 |
| 7,141,437 | B2 * | 11/2006 | Dvornic et al. .............. 436/532 |
| 7,238,842 | B2 * | 7/2007 | Wood et al. .................. 570/101 |
| 7,253,119 | B2 * | 8/2007 | Dutta .......................... 438/754 |
| 2002/0127623 | A1 * | 9/2002 | Minshull et al. ........... 435/7.92 |
| 2004/0072373 | A1 * | 4/2004 | Lin et al. ..................... 436/526 |
| 2005/0089926 | A1 * | 4/2005 | Taylor et al. .................. 435/7.1 |
| 2005/0106572 | A1 * | 5/2005 | Dvornic et al. ................. 435/6 |
| 2006/0008921 | A1 * | 1/2006 | Daniels et al. .............. 436/514 |
| 2006/0021938 | A1 * | 2/2006 | Diallo ......................... 210/638 |
| 2006/0024808 | A1 * | 2/2006 | Darzins et al. .............. 435/195 |
| 2006/0051878 | A1 * | 3/2006 | Dickson et al. ............. 436/518 |
| 2006/0199240 | A1 * | 9/2006 | Willner et al. ................. 435/14 |
| 2007/0086916 | A1 * | 4/2007 | LeBoeuf et al. ............... 422/58 |
| 2007/0141597 | A1 * | 6/2007 | Harmon .......................... 435/6 |

FOREIGN PATENT DOCUMENTS

WO 03/089599 * 10/2003

OTHER PUBLICATIONS

Berman, Harvey Alan et al, Biochemistry, 1980, vol. 19, pp. 2226-2235, Fluorescence Energy Transfer on Acetylcholinesterase: Spatial Relationship between peripheral site and active center.*
Bishop, WH et al, PNAS, vol. 77(4), pp. 1980-1982, Apr. 1980, Photodestruction of acetylcholinesterase.*
Ji, Xiaojun et al, J. Physical Chemistry B, 2005, vol. 109, pp. 3793-3799, (CdSe)ZnS Quantum Dots and Organophosphorus Hydrolase Bioconjugate as biosensors for detection of paraoxon.*
Li, Xiao-Hua et al, Development of Quantum Dots Modified Acetylcholinesterase Biosensor for the detection of Trichorfon, Electroanalysis, vol. 18 (22), Nov. 2006, pp. 2163-2167.*
Pardo-Yissar, Vered et al, Acetylcholine esterase labeled CdS Nanoparticels on elecrodes: Photoelectrochemical Sensing of the Enzyme Inhibitors, Journal of the American Chemical Society, vol. 125, pp. 622-623, 2003.*
Vamvakaki, Vicky et al, Biosensors and Bioelectronics, vol. 21, 2005, pp. 384-388, Fluorescence detection of enzymatic activity within a liposome based nanobiosensor.*
Snejdarkova, Maja et al, Electroanalysis, 2003, vol. 15(14), pp. 1185-1191, Acetylcholine biosensor based on Dendrimer layers for pesticides detection.*
Costa-Fernandez, Jose M. et al, Trends in Analytical Chemistry, vol. 25 (3), 2006, pp. 207-218.*
Simonian, AL et al, Analytica Chimica Acta, vol. 534, pp. 69-77, 2005, Nanoparticle-based optical biosensors for the direct detection of organophosphate chemical warfare agents and pesticides.*
Jin, Takashe et al, Chemical Communication, 2005, pp. 4300-4302, Amphiphilic p-sulfonatocalix[4]arene-coated CdSe/ZnS quantum dots for the optical detection of the neurotransmitter acetylcholine.*
Letant, Sonia E. et al, Chemical Commuication, 2005, pp. 851-853, Hydrolysis of acetylcholinesterase inhibitors-organophosphorus acid anhydrolase enzyme immobilization ofn photoluminescent porous silicon platforms.*
De Ferrari, Giancarlo V. et al, The Journal of Biological Chemistry, vol. 276(26), pp. 23282-23287, 2001, Thioflavin T is a fluorescent probe of the Acetylcholinesterase peripheral site that reveals conformational interations between the peripheral and Acylation sites.*
Layer, P et al, Molecular Pharmacology, vol. 12, pp. 958-965, Selective labeling of anionic binding sites of the Acetylcholinesterase from Torpedo califonica with a photoaffinity label, 1976.*
Yoon, Hyun C et al, Analytical Chemistry, vol. 72, pp. 922-926, Multilayered Assembly of Dendrimers with enzymes on Gold: Thickness controlled biosensing interface, 2000.*
Biosensor based on Self-Assembling Acetylcholinesterase on Carbon Nanotubes for Flow Injection/amperometric Detection of Organophosphate pesticides and Nerve Agents, Analytical Chemistry, 2006, vol. 78, pp. 835-843.*
Gill, R et al, Angew. Dhem. Int. Ed. 2008, vol. 47, pp. 1676-1679.*
Shcharbin, D et al, Effects of dendrimers on pure acetylcholinesterase activity and structure, Bioelectrochemistry, vol. 68, 2006, pp. 56-59.*

* cited by examiner

*Primary Examiner*—Mark Navarro
*Assistant Examiner*—Ginny Portner
(74) *Attorney, Agent, or Firm*—Lucas & Mercanti, LLP

(57) ABSTRACT

The present invention is directed to a quantum dot nanoparticle-based universal neurotoxin biosensor having three components (a) a dendrimer-encapsulated quantum dot nanoparticle; (b) acetylcholinesterase; and (c) an acceptor fluorophore, wherein the quantum dot nanoparticle and the acceptor fluorophore linked to the acetylcholinesterase.

13 Claims, No Drawings

QUANTUM DOT NANOPARTICLE-BASED UNIVERSAL NEUROTOXIN BIOSENSOR

CROSS-REFERENCE TO RELATED APPLICATION

This application claims the benefit of priority from U.S. Provisional Patent Application Ser. No. 60/781,096, filed Mar. 10, 2006, the contents of which are incorporated herein by reference.

BACKGROUND OF THE INVENTION

There is a pressing need for rapid and portable detection for neurotoxins, and though there has been considerable research in this field, there are very few sensors available to monitor an individual's exposure that can be produced and deployed on a large scale. In addition to monitoring of facilities, evaluation of individual exposure for those potentially exposed to neurotoxins, including farmers, first responders during a biochemical attack, and military personnel in at-risk areas, is a key issue for current biosensing technology.

A plethora of analytical methods are available to detect and quantitate neurotoxins. Neurotoxin quantitative analysis can be performed by detecting the products of toxin-specific enzymatic degradation or reaction with a toxin-specific reagent. (Enserink, M. Science, 2001, 294, 1266).

Alternative methods include monoclonal antibodies to detect a specific antigen by fluorescence visualization (Ong, et al., Analytica Chimica Acta, 2001, 444, 143), or monitor conformational changes in the antibody that occur as a result of antigen binding. (Goldman, et al., Anal. Chem. 2004, 76, 684). Monitoring conformational changes in antibody, however, requires high degree of specificity.

Fluorescence resonance energy transfer (FRET) can be an ideal method for monitoring changes in protein conformation because the effect is highly distance-dependent. (Haugland, R. P. Handbook of Fluorescent Probes and Research Products, Ninth Edition; Molecular Probes: Eugene, Oreg., 2002). FRET is a process that can occur between a donor-acceptor pair of fluorophores in which one fluorophore, when excited, transfers some of its energy without emitting light to a second fluorophore whose absorption wavelength overlaps the emission of the donor. FRET also depends on the quantum yield, relative donor-acceptor dipole orientations, and the ratio of FRET donors to acceptors.

Over the past years, organic dyes have been used extensively in FRET applications, but the requirements of FRET make matching a donor-acceptor pair difficult. (Lakowicz, J. R. Principles of Fluorescence Spectroscopy, 2nd ed.; Kluwer Academic: New York, 1999).

Many available methods of detecting neurotoxins are neurotoxin-specific. In situations at risks, there is a need for a universal neurotoxin detector. It is known that nearly all neurotoxins act on the acetylcholinesterase enzyme (AChE). Using such property of AChE, sensors based on the detection of AChE-catalyzed hydrolysis products are currently in development. Nevertheless, these methods rely on cumbersome and extensive instrumentation. (Pardo-Yissar, et al., J. Am. Chem. Soc. 2003, 125, 622; Zayats, et al., J. Am. Chem. Soc. 2003, 125, 16006).

In view of the forgoing, it would be desirable to provide a universal detector capable of rapid and universal detection with potential for mass production and deployment. The development of neurotoxin detection systems is crucial for human health and safety in agricultural, domestic, and defense areas.

SUMMARY OF THE INVENTION

In one preferred aspect of the invention, there is provided a biosensor having three components: (a) a dendrimer-encapsulated quantum dot nanoparticle; (b) acetyicholinesterase; and (c) an acceptor fluorophore, wherein the quantum dot nanoparticle and the acceptor fluorophore are linked to the acetyicholinesterase. More preferably, the quantum dot nanoparticle contains cadmium sulfide (CdS) as the donor fluorophore and the acceptor fluorophore is preferably a solfonated fluorescin derivative sold under trademark ALEXA FLUOR 488.

In some preferred aspects of the invention, the invention provides a neurotoxin dosimeter. The neurotoxin dosimeter contains the biosensor and means for allowing the biosensor to contact a sample containing a possible neurotoxin.

In another aspect of the invention, the invention provides a method of detecting a neurotoxin in a sample. The method includes providing a substrate containing the biosensor, applying a test sample to the substrate and measuring the change in fluorescence caused by applying the sample.

One of the advantages associated with the preferred aspects of the present invention is that the dendrimer-encapsulated quantum dot nanoparticles provide case of synthesis, stability, solubility and conjugation to biological molecules. Thus, the resulting biosensor can be used in situations requiring rapid, optical detection of neurotoxins.

Another advantage is the fact that nearly all neurotoxins act on acetylcholinestrase and thus, the biosensor containing acetylcholinesterase can act as a universal detector for various kinds of neurotoxins.

DETAILED DESCRIPTION OF THE INVENTION

The present invention relates generally to the biosensor capable of universal neurotoxin detection by mimicking the in vivo effect of neurotoxins on the acetylcholinesterase enzyme (AChE). Such biosensors confer the advantages of rapid exposure assay, mass production and deployment. In this novel biosensor, a neurotoxin is detected by monitoring the changes that occur in fluorescence resonance energy transfer (FRET) between a donor fluorophore and an AChE-acceptor fluorophore conjugate as a result of neurotoxin-AChE interaction.

One aspect of the invention provides a biosensor having three components (a) a donor fluorophore; (b) acetylcholinesterase; and (c) an acceptor fluorophore, wherein the donor fluorophore and the acceptor fluorophore are linked to the acetylcholinesterase. The biosensor allows detection of neurotoxins. Alternatively, AChE inhibitors can be detected by the biosensor described herein. For purposes of the present invention, it shall be understood that neurotoxins or AChE inhibitors encompass molecules that affect the conformation of AChE.

Some preferred aspects of the invention provide a biosensor having three components (a) a quantum dot nanoparticle as a donor fluorophore; (b) acetylcholinesterase; and (c) an acceptor fluorophore, wherein the quantum dot nanoparticle and the acceptor fluorophore are linked to the acetylcholinesterase.

More preferred aspects of the invention provide a biosensor having three components (a) a dendrimer-encapsulated quantum dot nanoparticle; (b) acetylcholinesterase; and (c) an acceptor fluorophore wherein the quantum dot nanoparticle and the acceptor fluorophore are linked to the acetylcholinesterase.

For purposes of the present invention, donor fluorophores encompass fluorophores and quantum dots described herein.

For ease of description and not limitation, it shall be understood that quantum dot nanoparticles shall be interchangeable with quantum dots.

For ease of description and not limitation, it shall be understood that quantum dots encompass dendrimer-encapsulated quantum dot nanoparticles.

Nearly all neurotoxins act on AChE and it is therefore of particular interest for the development of a universal detector for neurotoxins. Neurotoxins or AChE inhibitors that bind to AChE can change conformation of AChE upon binding. Neurotoxin detection can be accomplished by monitoring AChE inhibition via AChE conformation change. For example, neurotoxins such as VX, tabun, Sarin and Soman nerve gasses all affect the conformation of AChE.

Inorganic quantum-confined luminescent nanocrystals, known as quantum dots (QDs), have emerged as ideal donors in FRET applications: their high quantum yield and tunable size-dependent Stokes Shifts permit different sizes to emit from blue to infrared when excited at a single ultraviolet wavelength. (Bruchez, et al., *Science*, 1998, 281, 2013; Niemeyer, C. M *Angew. Chem. Int. Ed*. 2003, 42, 5796; Waggoner, A. *Methods Enzymol*. 1995, 246, 362; Brus, L. E. *J. Chem. Phys*. 1993, 79, 5566). In the past few years, hybrid organic/inorganic quantum dots based on a class of polymers known as dendrimers have been reported to hold great promise for use in biological labeling, imaging, and optical biosensing systems. (Lemon, et al., *J. Am. Chem. Soc*. 2000, 122, 12886). Unlike the traditional synthesis of inorganic quantum dots, the synthesis of these hybrid quantum dot nanoparticles does not require high temperatures or highly toxic, unstable reagents. (Etienne, et al., *Appl. Phys. Lett*. 87, 181913, 2005).

Dendrimers are a class of polymers composed of regularly branching monomers, synthesized in a highly controlled manner to tailor them to a specific size and shape (Fischer, et al., *Angew. Chem., Int. Ed*. 1999, 38, 884; Service, R. R. *Science* 1995, 267, 458; Tomalia, et al., *Angew. Chem. Int. Ed*. 1990, 29, 138); they take a spheroid shape as each new layer, or "generation," is added in a divergent synthesis. (Esfand, et al., *Drug Disc. Today*, 2001, 6, 427). This property gives dendrimers a maximal surface area to volume ratio with an exponentially increasing number of exposed functional groups. The multivalency of dendrimers makes them ideal for acting as platforms for conjugation to other molecules. Moreover, the dendrimer's branches are spaced widely enough to allow small molecules, such as solvents and ions to enter. Despite the large size and molecular weight of dendrimers, their branches and surface groups can be tailored to render them soluble in biological media. (Sooklal, et al., *Adv. Mater*. 1998, 10, 1083). Thus, dendrimer-encapsulated quantum dot nanoparticles provide the advantage of ease of synthesis, stability, solubility and conjugation to biological molecules via surface derivatization of the dendrimers.

The quantum dot nanoparticles which have recently been synthesized provide a larger number of surface groups available for conjugation than previously achieved. These materials were synthesized by encapsulating $Cd^{2+}$ and $S^{2-}$ ions within poly(propylenimine) dendrimers with a diaminobutane (DAB) core. The resulting quantum dot nanoparticles possess properties that made them ideal for sensor development; they retain their optical properties after long-term storage and after being spin-coated onto substrates to create solid-state thin-films (Potasek, et al., *Proc. of SPIE* Vol. 6129, 61290H, 2006).

The dendrimer with multiple layers of monomers capable of encapsulating the quantum dots can be utilized for the quantum dot nanoparticles. In the present invention, the preferred dendrimer is polypropylenimine tetrahexacontaamine dendrimer, a fifth generation poly(propylenimine) diaminobutane core dendrimer. The fifth generation dendrimer has five layers of monomers. Alternatively, different generations of poly(propylenimine) dendrimers can also be utilized. Among various generations of the poly(propylenimine) dendrimers are "DAB" dendrimers including generations 1 through 7, known as "DAB 4", "DAB 8", "DAB 16", "DAB 32", "DAB 64", "DAB 128" and "DAB 256" which are marketed under trade name ASTRAMOL™. In addition, a person of ordinary skill will appreciate alternative suitable dendrimers, such as poly(amidoamine) dendrimer. Various generations of the poly(amidoamine) dendrimers, for example, generations 1 through 10 are known as "PAMAM" dendrimers and marketed under trade name STARBURST™.

In the present invention, a non-limited list of quantum dots includes cadmium sulfide (CdS), cadmium selenide (CdSe), zinc sulfide (ZnS), zinc oxide (ZnO), lead sulfide (PbS), zinc selenide (ZnSe), GaAS and InP. (Lakowicz et al. *Analytical Biochemistry*, 2000, 280:128-136). Alternative suitable donor fluorophores will be apparent to those of ordinary skill without undue experimentation. A person of ordinary skill will also appreciate alternative quantum dots. In one preferred aspect of the invention, the quantum dot is preferably CdS.

Alternatively, other commercially available quantum dot nanoparticles can be used for the biosensors described herein. For example, quantum dots currently marketed by Evident Technologies, Inc. can be used. The quantum dot nanoparticles have various surface groups available for conjugating to proteins. These groups include but are not limited to thiol, amine, nitrile, phosphine, phosphine oxide, phosphonic acid, carboxylic acid or others ligands. See U.S. Pat. No. 6,872, 450. Moreover, tunable emission wavelength of the quantum dots allows various pairs of a donor fluorophore and an acceptor fluorophore. Among alternative quantum dots are cadmium selenide (CdSe)/zinc sulfide (ZnS) core/shell quantum dot and InGaP/ZnS quantum dots.

In one preferred aspect of the invention, the quantum dot nanoparticle is a dendrimer-encapsulated quantum dot nanoparticle. In one preferred embodiment of the invention, the quantum dot nanoparticle is a polypropylenimine dendrimer-encapsulated Cd/S quantum dot nanoparticle.

One of the requirements for the acceptor fluorophore is that the acceptor fluorophore whose absorption wavelength does not overlap the absorption wavelength of the donor fluorophore be able to absorb emission of the donor fluorophore land thus emit its own emission.

In certain aspects, the acceptor fluorophore is capable of absorbing emission of the donor fluorophore. In one particular embodiment of the invention, a solfonated fluorescin derivative sold under trademark ALEXA FLUOR 488 is preferred. Alternatively, non-fluorescent acceptors of energy to "dim" the biosensor's emissions could also be utilized, or another fluorescent quencher matched with the donor fluorophore's emission wavelength could be used as the acceptor fluorophore. It will be appreciated that any one of the art recognized fluorophores that absorbs the donor fluorophore's emission can be used as an acceptor fluorophore. A non-limiting list of alternative acceptor fluorophores includes Dabsyl, Dabeyl and QSY35.

In one particular embodiment of the invention, the donor-acceptor pair is preferably CdS and a solfonated fluorescin derivative sold under trademark ALEXA FLUOR 488.

About three or four ∈-amino groups of Lysine of acetylcholinesterase are available to bind the donor fluorophore including quantum dots. In certain aspects of the invention, a ratio of the quantum dot nanoparticle and the acetylcholinesterase is from about 1:1 to about 1:3. In particular aspects of the invention, a ratio of the quantum dot nanoparticle and the acetylcholinesterase is preferably about 1:1. Multiple crosslinking is not favored due to steric hinderance and entropy of large molecules.

In one particular embodiment of the present invention, the biosensor contains AChE conjugated to a $5^{th}$ generation polypropylenimine dendrimer (polypropyleneimine tetrahexacontaamine, G1.0, 1,4-diaminobutane core sold under the trademark DAB-AM-64 encapsulated cadmium sulfide quantum dot and a solfonated fluorescin derivative sold under trademark ALEXA FLUOR 488.

In the formation of the quantum dot nanoparticle and acetylcholinesterase conjugate, either of the components can be modified as shown in Examples. When the acetylcholinesterase and acceptor fluorophore conjugate is formed, both or either of the components can also be modified. In the present invention, suitable linkers known to those of ordinary skills in the art can be used for conjugating the donor fluorophore and the acceptor fluorophore to AChE. Modification with linkers can be done by methods known in the art without undue experimentation. Artisans in the art can appreciate suitable modifiers or linkers for forming the conjugate. In one preferred aspect of the invention, the acetylcholinesterase in modified with SATA (N-Succinimidyl-S-acetylthioacetate) to produce sulfhydryl groups and the donor fluorophore is modified with maleimide in Example 1. In Example 2, the native ε-amino groups of AChE reacted with modified acceptor fluorophore.

The acetylcholinesterase bridge in the biosensor creates about ~60 Å space between the quantum dot nanoparticle and the acceptor fluorophore. Since FRET occurs on average across a distance of about 20-100Å, a person with ordinary skill in the art can appreciate various combinations of modifiers or linkers that allow such space between the quantum dot nanoparticle and the acceptor fluorophore.

In some aspects of the invention, an average distance between the donor fluorophore and the acceptor fluorophore is about 20-100 Å, and preferably, about 60 Å.

In one preferred aspect of the invention, a ratio of the acetylcholinesterase and the acceptor fluorophore is from about 1:1 to about 1:3. As shown in Example 3, about three or four ε-amino groups of lysine of acetylcholinesterase are available to bind the acceptor fluorophore without affecting surface exposure, potential negative effect on backbone and active site conformation, and active site shielding of acetylcholinesterase. More preferably, the ratio of the acetylcholinesterase and the acceptor fluorophore is about 1:2.

In some preferred aspect of the invention, the invention provides a neurotoxin dosimeter. The neurotoxin dosimeter contains the biosensor and means for allowing the biosensor to contact a sample containing a possible neurotoxin or acetylcholinesterase inhibitor. In some embodiments of the dosimeter, the biosensor is incorporated into a hydrogel matrix.

In another aspect of the invention, the invention provides a method of detecting a neurotoxin or an acetylcholinestrase inhibitor in a sample. The method includes providing a substrate containing the biosensor, applying a test sample to the substrate and measuring the change in fluorescence caused by applying the sample.

EXAMPLES

The following examples serve to provide further appreciation of the invention but are not meant in any way to restrict the effective scope of the invention.

Instrumentation and Facilities:

Fluorescence spectra are taken with a Perkin-Elmer PS-50B Luminesence Spectrometer running Fluoresence Luminesence Data Manager on an IBM PS/2 computer. UV-visible absorption spectra are taken using a Hewlett-Packard 8452A Diode Array Spectrophotometer controlled by a Hewlett-Packard Vectra XL computer running HP 845x UV/Vis. The path length of fluorescence and UV-visible cuvettes (Fisher Scientific) is 1 cm. Molecular models are constructed using MacSpartan Pro. (Wavefunction Inc., Irvine, Calif., USA). Visualization and distance calculations are performed on proteins and protein conjugates using the PyMOL Molecular Graphics System. (DeLano Scientific, San Carlos, Calif., USA). All modeling work is performed on an Apple Power Macintosh G4 running Mac OS X, 10.3.6.

Chemicals:

Poly(propylenimine) dendrimers with a diaminobutane core DAB-AM-64, Polypropylenimine tetrahexacontaamine Dendrimer, Generation 5.0), cadmium (II) nitrate, and sodium sulfide are available from Aldrich. Anhydrous dichioromethane is available from Aldrich and is degassed before use. All other solvents are of reagent grade.

All stock solutions are prepared under argon in dry conditions. DAB dendrimer is dissolved in dichloromethane to form a $4.32 \times 10^{-5}$ M solution and serial dilutions are performed until a final concentration of $1.73 \times 10^{-6}$ M is reached. Separate solutions of cadmium (II) nitrate and sodium sulfide in methanol are prepared, both with concentrations of $3.84 \times 10^{-3}$ M.

Example 1

A. Modification of Quantum Dot Nanoparticle

The amine surface of the quantum dot nanoparticle including dendrimer-encapsulated quantum dots is modified with a linking agent such as Sulfo-SMCC (Sulfosuccinimidyl 4-N-maleimidomethyl cyclohexane-1-carboxylate) to form a maleimide-activated quantum dot. Any excess reagent is removed by size-exclusion chromatography, a commonly-employed technique to separate the components of the reaction mixture. Methods for encapsulating quantum dots with dendrimers are described in, for example, Lemon et al. (*J. Am. Chem. Soc.*, 2000, 122:12886), the contents of which are incorporated herein by reference.

B. Modification of Acetylcholinesterase ε-amino groups of Lysine Residues

The epsilon amines of the acetylcholinesterase (AChE) enzyme, obtained as recombinant human form or isolated from *Electrophorus electricus* or bovine crythrocytes, is modified with SATA (N-Succinimidyl-S-acetylthioacetate) to provide sulfhydryl groups. Any excess reagent is removed by size-exclusion chromatography.

C. Formation of Quantum Dot Nanoparticle-AChE Conjugate

Maleimide-activated QD is reacted with the sulfhydryl-modified AChE for a limited time to prevent multiple QDs from attaching to multiple proteins. Multiple crosslinking is not favored due to steric hinderance and entropy of large molecules. The reaction is halted by separation using size-exclusion chromatography.

D. Formation of Quantum Dot Nanoparticle-AChE-ALEXA FLUOR Conjugate

An excess of ALEXA FLUOR® 488 C5 maleimide dye is reacted with the desired QD-AChE complex, previously isolated by size-exclusion chromatography, on which reactive suithydryl are still present. The biosensing molecule (QD-ACbE-dye) is isolated by size-exclusion chromatography. Performing any reactions involving ALEXA FLUOR® 488 in a darkroom (under red light) or in complete darkness increases the yield of the product.

Alternatively, steps C and D could he combined. A mixture of the maleimide-activated QD and the maleimide-functionalized ALEXA FLUOR® 488 fluorescent dye could be added in one step. By controlling the proportions of the QD and the dye, it could be possible to restrict the binding to 1 QD per protein, with all of the other sites for binding on the protein being taken by the dye.

Example 2

Chemicals:

Acetyicholinesterase is available from Fluka (1 mg, dialyzed powder, 850 units/mg) and is used without additional purification. A solfonated fluorescin derivative sold under trademark ALEXA FLUOR 488 ($AF_{488}$ carboxylic acid, TFP tester, bis-triethylammonium salt), concentrated phosphate-buffered saline (PBS) solution, and Bio-Rad BioGel P-30 Fine size exclusion purification resin are available from Molecular Probes. (Invitrogen Corp., Eugene, Oreg., USA). All other materials and reagents, including other necessary buffers, are available from Fisher Scientific.

All stock solutions are prepared in deionized $H_2O$. A 2 mg/ml solution of AChE is prepared in a 0.1 M sodium bicarbonate buffer solution in deionized $H_2O$. Concentrated PBS is diluted to form an elution buffer of 0.1 M potassium phosphate and 0.02 M sodium azide. A 0.0025 M acetylcholine-salt-gelatin solution of acetylcholine chloride, 0.1 M sodium chloride, 0.02 M magnesium chloride, and 0.005% gelatin is prepared as well as a 0.02 N solution of potassium hydroxide.

A. Modification of Acetyicholinesterase ε-amino groups of Lysine Residues with ALEXA FLUOR TFP ester Standard dye-labelling procedures are followed to label the ε-amino groups of lysine residues. A Bio-Rad BioGel P-30 Fine size exclusion chromatography column is packed in PBS solution and allowed to equilibrate for two hours. 500 μl of AChE solution is transferred to a vial containing 500 μg of $AF_{488}$ and stirred in the dark at room temperature for 3 hours, then loaded onto the BioGel size-exclusion column. The column is eluted with PBS and the progress of the labeled protein and unbound dye is monitored with a 354 nm UV lamp. The fluorescence and UV-visible spectra are taken of the dye-labeled protein fraction, which is subsequently stored in the dark at 4° C.

Though the $AF_{488}$ dye chosen for the biosensor has been used extensively in protein labeling applications, it has not previously been used to label AChE. With this consideration in mind, AChE is labeled with an ε-amino-reactive tetrafluorophenol (TFP) ester of $AF_{488}$ and the activity of the purified AChE-$AF_{488}$ conjugate is assayed. Purification via size-exclusion chromatography is efficient: two distinct fluorescent bands are observed and collected separately. The first band contained the protein-dye conjugate and is confirmed by UV-visible absorption, with characteristic protein absorption observed at 250 to 300 nm and characteristic $AF_{488}$ absorption at 492 nm. Using the known molar absorptivity values for both AChE and $AF_{488}$, 0.565 g of AChE is labeled (56.5% yield) and the number of bound dyes per protein is calculated to be 5 (±1).

Example 3

A. Modeling of Optimal Conjugation Sites among ε-amino groups of Lysine Residues of Acetylcholinesterase The structure of Electrophorus Electricus Acetylcholinesterase was obtained from the Protein Data Bank (1C2B) and was previously determined by Boume, et al. (*J.Biol.Chem.* 1999, 274, 30370). The active site of AChE is located within the peptide sequence using previously reported search algorithms. (Wallace, et al., *Prot Sci.* 1997, 6, 2308). Models of $AF_{488}$ (ALEXA FLUOR 488 carboxylic acid, TFP ester) and DAB dendrimer (DAB-AM-64, Polypropylenimine tetrahexacontaamine Dendrimer, Generation 5.0) were generated based on published structural data. (U.S. Pat. No. 6,716,979; Publication of DSM Research, Geleen, the Netherlands).

B. Changes in Protein Conformation Due to Selective Lysine Residue Modification

Structurally-exposed lysine residues of proteins are ideal for conjugation because of their long, flexible carbon chains and exposed ε-amino groups. To determine the lysine residues that could be modified with minimal interference to AChE structure and function, computational methods were employed to predict conformational changes that would result from conjugation to CdS-DAB QDs and $AF_{488}$. Using MacSpartan Pro, models of the proposed amide linkage between AChE and $AF_{488}$ as well as the linkage between AChE and CdS-DAB QDs were constructed, and force field calculations of the entire AChE structure and of the proposed modified lysine residues were performed using The Hetero-Compound Information Centre server (HIC-Up). (Kleywegt, et al., *Acta Cryst.* 1998, D54, 1119). Force-field interactions between the protein and proposed conjugate were calculated using the Merck Molecular Force Field method. (Halgren, et al., *J. Comp. Chem.* 1996, 17, 587). The enclosure of specific lysine residues was determined by calculating the protein pockets within AChE. (Liang, et al., *Prot. Sci.*, 1998, 7, 1884). Using MacPyMOL, all data from the previous calculations were compiled land visualized. The impact of conjugation at specific lysine residues on the conformation and shielding of the active site was determined using a series of distance calculations between active site "checkpoint" atoms and protein surface calculations within MacPyMOL.

The primary amine conjugation effects on acetylcholinesterase conformation and function such as backbone and active site conformation, and active site shielding of a conjugate for each lysine residue are calculated using computational modeling. The computational modeling data shows that lysine residues at 23, 348, 496, and 538 positions can be candidates for the desired conjugation. Minimal interference was observed by attaching conjugates at LYS-23 and LYS-538. Based on this information, a model of the entire biosensing assembly could be constructed.

Example 4

Enzyme Activity Assay of AChE-$AF_{488}$ Conjugate:

Acetylcholine-salt-gelatin solution stock solution (15 ml) was placed in a flask below a burette with KOH solution. 250 μl of AChE-$AF_{488}$ conjugate (0.125 mg AChE) was added to the flash and the pH of the solution in the flask was returned to 7.0. The amount of 0.01 N KOH necessary to neutralize the acetic acid produced by acetylcholine hydrolysis was determined by titration and used to calculate the rate of AChE-$AF_{488}$ activity.

Once it was established that AChE could be easily conjugated to $AF_{488}$ using standard dye-labeling protocols, it was necessary to determine the effect of dye conjugation on AChE activity. 20.2 ml of KOH solution was required each minute to neutralize the acid produced by AChE-catalyzed hydrolysis of acetylcholine. Given the known volume and normality of the KOH added as well as the amount of enzyme in solution, the enzymatic activity of the AChE-$AF_{488}$ conjugate was calculated to 820 activity units per 1 mg of protein (820 U). AChE, which has a native activity of 1000 U (Sigma-Aldrich, St. Louis, Mo., USA), therefore had only an 18% decrease in activity after being bound to $AF_{488}$. These results confirm the feasibility of using AChE-dye conjugates in biosensing applications—AChE must retain its enzymatic function and conformation in order for the proposed biosensor to operate.

Example 5

Preparation of a Badge Dosimeter:

The novel biosensing molecule described in Examples is ideally suited to monitoring individual exposure. A badge dosimeter of the biosensing molecule assembly is constructed in the following manner: (i) synthesized the biosensing molecule in bulk; and (ii) coating the biosensing molecule onto a commercially UV-transparent substrate, such as a UV-transparent plastic.

Alternatively, the biosensing molecule is incorporated into a hydrogel matrix deposited on the substrate.

The substrate with the biosensing molecule assembly is affixed to a badge with a computer-readable ID number, such as barcode or smart chip. The substrate can be attached to an existing employee ID card or to its own badge. Alternatively, the substrate with biosensing molecule assembly can be attached to a badge along with other separately-developed sensors to create a multiplexed sensing array. Other such means for allowing the biosensor to come into contact with ambient air or samples which may contain a neurotoxin or biohazard will be apparent to those of ordinary skill.

In the event of a terrorist attack, an individual would attach this badge to their uniform so that the biosensor is exposed to whatever they are exposed to.

A simple device composed of commercially available parts (UV light source, array of photodetectors for emission wavelengths of the FRET acceptor fluorophore in the biosensing assembly, and barcode/smart chip reader) can be constructed to measure the fluorescence of the biosensing molecule within the biosensing assembly. The fluorescence emission of the neurotoxin-exposed sensor is compared to the emission of a reference sample to determine neurotoxin exposure. The exposure data is associated with the ID number from the barcode/smart chip and reported immediately on a digital display and stored in a database for later access and reporting.

Alternatively, the device can deposit a small drop of solvent to dissolve any gel layer and ensure contact between the sensing molecule and the captured neurotoxin.

Example 6

Distributed Facility Monitoring:

The badge dosimeter described herein is also well-suited to distributed facility monitoring in which a large number of enclosed spaces can be monitored simultaneously. In this arrangement, the biosensing assembly is coated onto a substrate or incorporated into a hydrogel matrix deposited on the substrate and integrated with the device described herein to continuously monitor the fluorescence of the molecule. Integrated with the facility's existing emergency response system, the distributed sensors allow for the redirection of airflow to minimize the spread of a biological or chemical agent, the initiation of 'intelligent' evacuations, and the activation of purification systems.

Example 7

Applicant incorporates herein by reference "Covalent Assembly of a Nanodot-Based Neurotoxin Biosensor" which was presented at the Intel Science Talent Institute at the National Academy of Sciences in Washington, D.C. on Mar. 12, 2005.

Each of the patent and publications mentioned in this application is incorporated herein by reference.

What is claimed is:

1. A biosensor for detecting neurotoxins or acetylcholinesterase inhibitors, comprising:
   (a) a donor fluorophore, wherein the donor fluorophore comprises a dendrimer-encapsulated quantum dot nanoparticle and wherein the dendrimer is a polypropylenimine dendrimer or a polyamidoamine dendrimer;
   (b) acetylcholinesterase; and
   (c) an acceptor fluorophore,
   wherein the donor fluorophore and the acceptor fluorophore are linked to the acetylcholinesterase.

2. The biosensor of claim 1, wherein the dendrimer-encapsulated quantum dot nanoparticle comprises cadmium sulfide.

3. The biosensor of claim 1, wherein the quantum dot nanoparticle is selected from the group consisting of cadmium selenide (CdSe) and cadmium sulfide (CdS).

4. The biosensor of claim 1, wherein the acceptor fluorophore is capable of absorbing emission of the donor fluorophore.

5. The biosensor of claim 1, wherein the acceptor fluorophore is a sulfonated fluorescein derivative.

6. The biosensor of claim 1, wherein the donor fluorophore is a polypropylenimine tetrahexacontaamine dendrimer-encapsulated cadmium sulfide quantum dot and the acceptor fluorophore is a solfonated fluorescin derivative.

7. The biosensor of claim 1, wherein the ratio of the quantum dot nanoparticle and the acetyleholinesterase is about 1:1.

8. The biosensor of claim 1, wherein the ratio of the acetyicholinesterase and the acceptor fluorophore is from about 1:1 to about 1:3.

9. The biosensor or claim 1, wherein the ratio of the acetyleholinesterase and the acceptor fluorophore is about 1:2.

10. The biosensor of claim 1, wherein an average distance between the donor fluorophore and the acceptor fluorophore is about 20-100 Å.

11. The biosensor of claim 1, wherein an average distance between the donor fluorophore and the acceptor fluorophore is about 60 Å.

12. A neurotoxin dosimeter comprising the biosensor of claim 1 and means for allowing the biosensor to contact a sample which may contain a neurotoxin or an acetyleholinesterase.

13. The neurotoxin dosimeter of claim 12, wherein the biosensor is incorporated into a hydrogel matrix.

* * * * *